United States Patent [19]

Smith

[11] 4,281,389
[45] Jul. 28, 1981

[54] PACING TIMER MOUNTING ARRANGEMENT

[76] Inventor: Kent G. Smith, 51 W. 83rd St., New York, N.Y. 10024

[21] Appl. No.: 51,135

[22] Filed: Jun. 22, 1979

[51] Int. Cl.³ .................... G06F 15/20; A41D 19/00
[52] U.S. Cl. ...................................... 364/569; 2/160;
364/415; 364/561
[58] Field of Search ............... 364/561, 569, 415, 417;
2/160; D2/364, 368, 373

[56] References Cited

U.S. PATENT DOCUMENTS

| 2,103,711 | 12/1937 | Cole | 2/160 |
| 3,124,806 | 3/1964 | Campbell et al. | 2/160 |
| 3,629,867 | 12/1971 | Taylor | 2/160 |
| 3,638,011 | 1/1972 | Bain et al. | 2/160 X |
| 4,053,755 | 10/1977 | Sherrill | 364/561 |

*Primary Examiner*—Jerry Smith
*Attorney, Agent, or Firm*—Kenyon & Kenyon

[57] ABSTRACT

A digital pacing timer mounting arrangement which includes a glove piece to be worn by the runner and including a mounting means on the glove for detachably mounting a pacing timer having a plurality of controls with the timer being located between the knuckles of the index finger and thumb with the face of the timer including a display and the reverse side of the timer including an input.

12 Claims, 7 Drawing Figures

PACING TIMER MOUNTING ARRANGEMENT

CROSS-REFERENCE TO RELATED APPLICATION

This application is related to applicant's commonly owned Ser. No. 51,016 entitled "Digital Pacing Timer" and filed on the same date as the instant application.

BACKGROUND AND SUMMARY OF THE INVENTION

This invention is related to a pacing timer mounting arrangement whereby a runner's pacing timer, which includes both audible signal and visual display means for communicating information to the runner, is mounted on a runner's hand in such a fashion so as to be easily viewable and so that controls located on the pacing timer can be manipulated with convenience.

The pacing timer mounting arrangement in accordance with this invention includes a glove piece having openings for the runner's index finger and thumb and includes a mounting means, for example, a pad located on the glove to which the pacing timer is detachably affixed. The mounting means is located between the base of the knuckles of the runner's index finger and thumb, so that, when the runner's arms are brought up to a position comfortable for running long distances, the visual display of the pacing timer will be easily visible to the runner without requiring the twisting or distorting of the runner's hand or arm.

There is provided a keyboard for entering data into the pacing timer and, since this keyboard is used before a run and is not used during the course of a run, the keyboard is conveniently located on the reverse side of the pacing timer adjacent the mounting means located on the runner's glove. Since the keyboard is located in an inaccessible position facing the mounting means when the unit is affixed to the glove, there is effected a saving of runner accessible space on the unit's face side whereby more runner accessible controls can be included and more space left for display.

The controls which are activated during the course of a run are located on the periphery of the pacing timer so that they can be easily located by the fingers of the opposite hand and activated independently of each other even while the run is in progress. In accordance with another aspect of my invention, these controls have different shapes so as to be readily identifiable by touch alone, and are so shaped that the finger or fingers used to operate them will not slide off. Furthermore, the edges of the controls are rounded to eliminate chance of injury.

In accordance with another aspect of my invention, a speaker is provided in the face of the pacing timer for providing the runner with an audible tone corresponding to the runner's stride frequency.

The pacing timer mounting arrangement is, therefore, adapted to provide the runner with a visual display conveniently positioned for viewing during running and provides a compact and efficient arrangement of controls in that those controls which are not utilized during the course of a run are located on an inaccessible side of the unit thereby leaving more room for the controls and display which are needed during the course of the run.

In one embodiment of my invention, described more fully below, elastomeric adhesive material is provided in the form of a pad on the glove and is also detachably affixed to the reverse side of the pacing timer over the keyboard so that the device can be affixed to the mounting pad by the simple application of pressure.

DETAILED DESCRIPTION OF THE DRAWINGS

Figure 1:
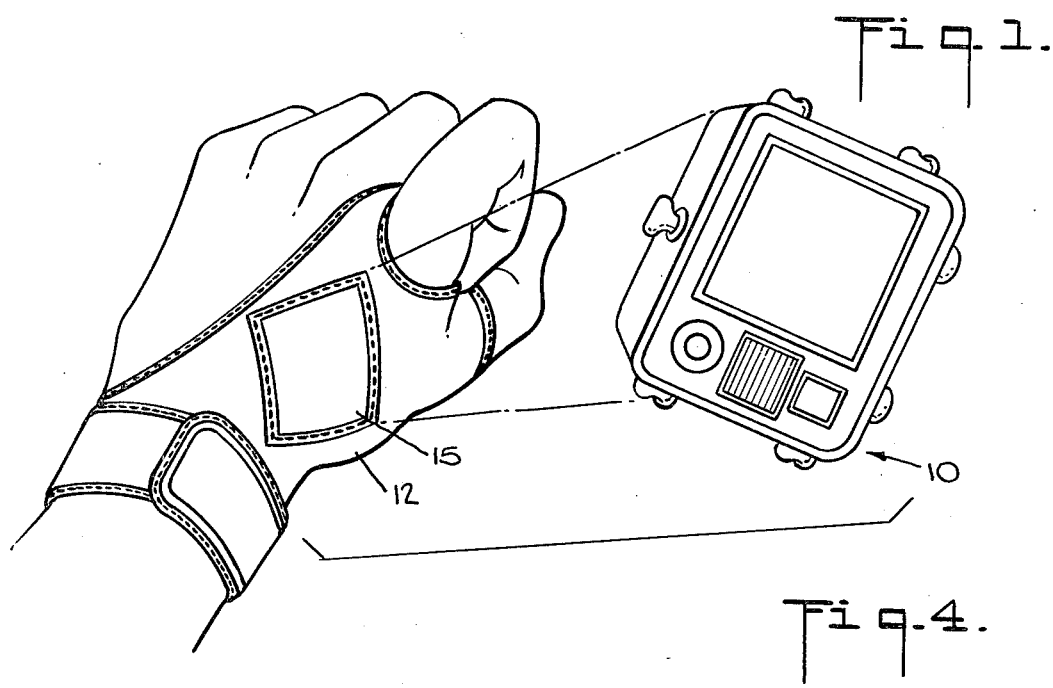
FIG. 1 shows a perspective view of the pacing timer and the glove piece to which the timer is detachably affixed.
Figure 6:
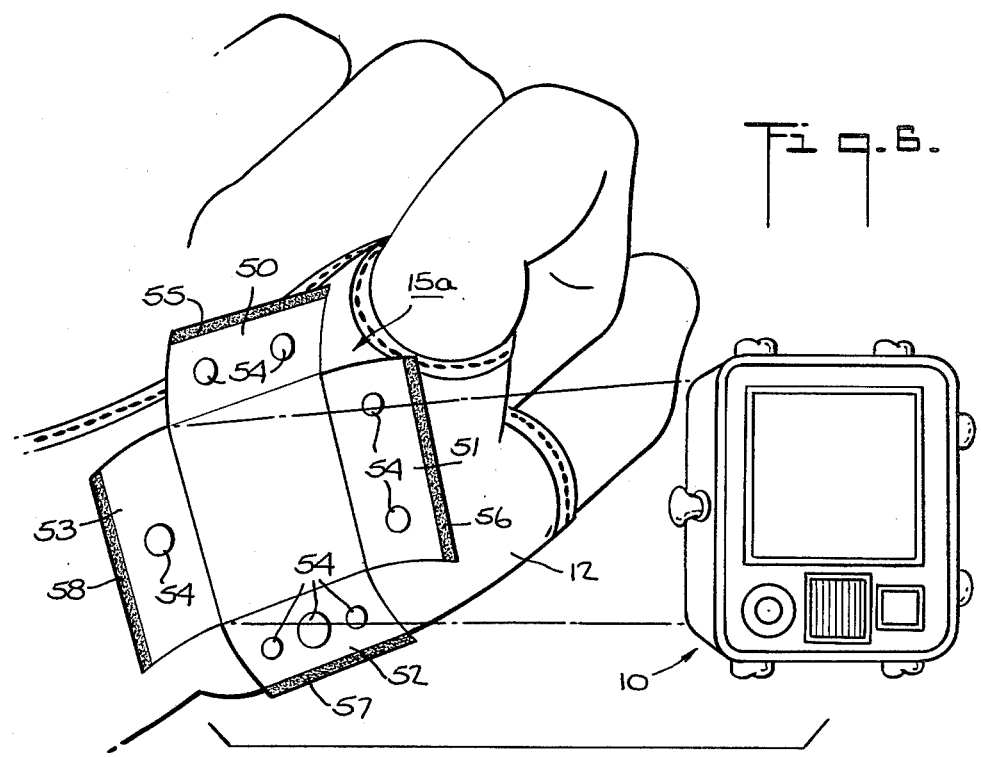
FIG. 6 shows another embodiment of mounting means in accordance with my invention.
Figure 7:
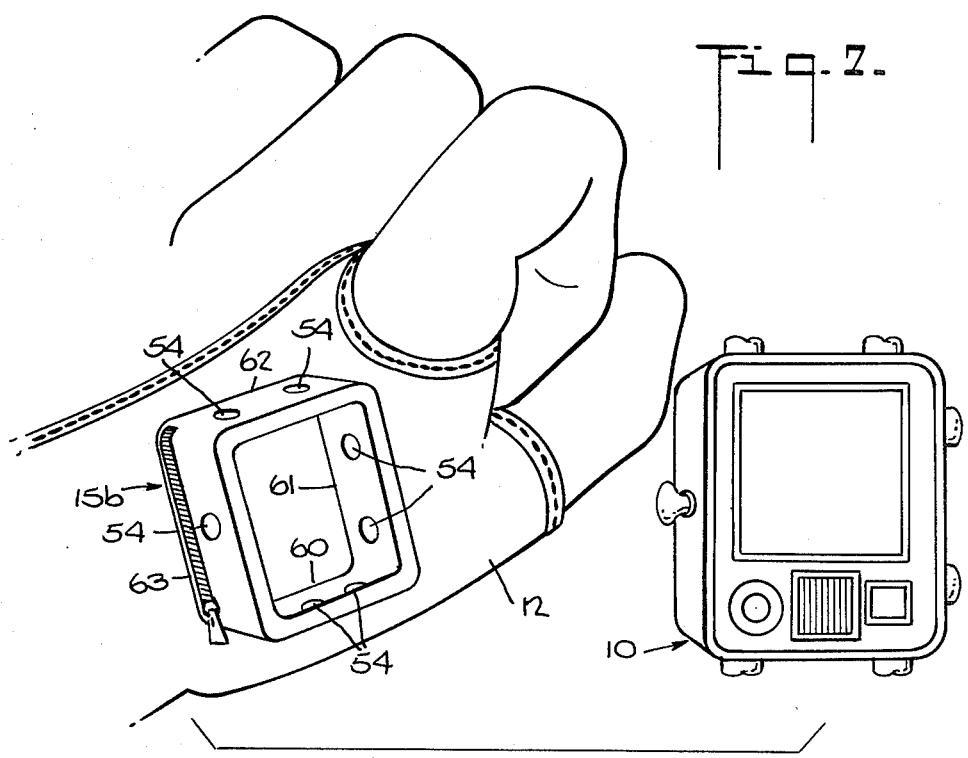
FIG. 7 shows another embodiment of mounting means in accordance with my invention.

The digital pacing timer mounting arrangement constructed in accordance with the teachings of this invention as seen in FIG. 1 includes the detachable pacing timer 10, the construction and operation of which are described in detail in my above-mentioned copending application, and a mounting means 15 in the form of a mounting pad located on glove 12. FIGS. 6 and 7 discussed in detail below depict other embodiments of mounting means 15 constructed in accordance with my invention.

Mounting pad 15 (FIG. 1) is located on the back of the glove 12 at a position which is forward of the runner's wrist and between the knuckle at the base of the thumb and the knuckle at the base of the index finger. The positioning of the pacing timer 10 on the mounting pad 15 between the base of the knuckles of the index finger and thumb assures that the pacing timer will be at a position of maximum visibility to the runner when he is in the running position. A long-distance runner will generally carry his arms with the elbows bent at the runner's sides so that the hands of the runner are pointing in a forward direction. The hands of a running person are generally held so that if the runner should look at his left hand he would see the region between the bases of the knuckles of the index finger and the thumb and forward of the wrist.

It is important to note that the usual runner does not carry his hands in such a way that he could see the back of his wrist at the location where a usual wristwatch would normally be carried. In order to see the usual wristwatch location at the wrist it would be necessary to twist the hand into an unnatural and uncomfortable position with the palm facing downward and the elbow extendng in an outward lateral direction which would be distracting to a runner particularly if the movement had to be repeated periodically since it is a movement which requires cross motion relative to his forward movement. The mounting pad 15 is large enough so as to allow the pacing timer 10 to be located at a number of different positions so that the pacing timer can be affixed to the mounting pad 15 at a particular location for maximum visibility in correspondence with the manner in which the individual runner holds his hands during running.

The mounting pad 15 is preferably provided with an elastomeric type adhesive of nylon or glass fiber. Such adhesives are well known and are readily available on the market. The glove 12 is preferably made of nylon and includes openings for the thumb and index finger with the rest of the fingers being free as seen in FIG. 1. The glove 12 would be affixed at the wrist by means of an appropriate attaching means such as buttons, snaps, or, preferably, an elastomeric type adhesive such as that used for the pacing timer mounting pad 15. In lieu of the elastomeric adhesive, the mounting pad can include other attaching means such as straps, snaps, loops or the like.

Because of the position of the pacing timer 10 between the bases of the knuckles of the index finger and thumb, it is easily visible to the running person without requiring that the runner distort his hand position for viewing the pacing timer 10. Preferably, the pacing timer 10 is worn on the hand and is not carried within the hand, since it is then possible for the runner to relax his finger muscles during the race and to be able to stretch and move his fingers during a long race to a greater degree than if the pacing timer were mounted in the palm area of the hand. However, it is within the scope of my invention to utilize any of the constructions shown in the Figures to mount the pacing timer in the palm region of the glove piece.

Figure 2:
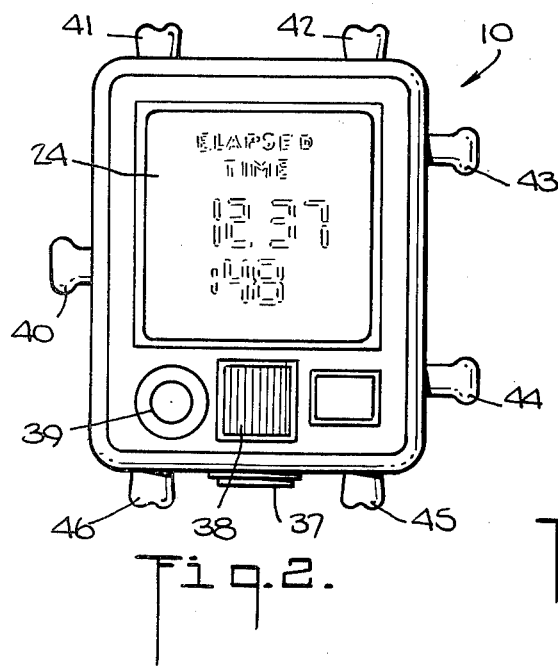
FIG. 2 shows a view of the face of the pacing timer.

Further details of the pacing timer 10 are seen in FIGS. 2 through 5. As is seen in FIG. 2, the pacing timer includes a digital display 24 for indicating on demand or automatically various data of relevance to the runner's performance. Although the particular data displayed by unit 24 and how they are calculated form no part of this invention, data which are of interest to the runner and which can be displayed by unit 24 include distance covered, speed, elapsed time, the amount of time by which the runner is ahead of or behind a present target time and/or the runner's pulse rate. The calculation of such information is described in my above-mentioned copending application.

FIG. 2 also shows a speaker 38 which is used to emit striding tones to the runner. The striding tones can be calculated within the pacing timer and effectively give the runner an indication of the speed at which he is running or the speed at which the runner should be running. The tone emitted by speaker 38 can be calculated by considering such factors as the runner's stride length at various speeds, the length of the race of "split" (intermediate distance goal in a race) and the amount of time which the runner wishes to allow himself for any particular split.

It is contemplated that there be provided a plurality of conveniently accessible controls whose functions are described in my copending application located on the face and at the periphery of the pacing timer 10. The face of the pacing timer 10 includes start-stop control 39; periphery controls are indicated at 40 through 46. Actuation of control 40 reduces the preset race time by a predetermined amount, for example, 6 seconds. The internal circuitry of the pacing timer 10 is programmed to increase the rate of the stride tone of speaker 38 to a rate at which the runner must proceed to complete the race within the preset race time as reduced by control 40.

Control 41 actuates the digital display 24 to read out the total distance which the runner has run up to the instant when control 41 is depressed. Control 42, when depressed, causes the current speed of the runner to be displayed on display 24 and causes the striding tones to be sounded continuously if control 42 is held down for two seconds.

Speed control 43 may be moved in an upward or downward direction to cause an incremental change in the stride tone rate corresponding, for example, to an increase or decrease in speed of six seconds per mile (or six seconds per kilometer). Speed control 43 would be activated by the runner if, for example, he found that he could not keep up the preselected running rate, and wished to slow down, or if the runner decided to proceed through the race at a faster rate. By repetitively depressing control 43 in either the upward or downward direction, the runner can find his most comfortable rate.

Control 44 when activated in an upward direction would cause the digital display 24 to read out the total elapsed time since the start of the race. By actuating control 44 in a downward direction, the display 24 presents the amount of time the runner is ahead or behind in his preset race time target, taking into account the actual distance which the runner has run up to the instant when the control 44 is activated.

Control 45 is a "catch-up" control which will cause the pacing unit to calculate a new speed for the runner which will enable the runner to catch up to his preprogrammed target time for the split. Control 46 is a pass split marker control which is activated each time the runner finishes a particular split (i.e. portion of a race); actuation of control 46 causes the pacing time to reset a number of its circuit units and process the data regarding the next split to be run.

Figure 3:
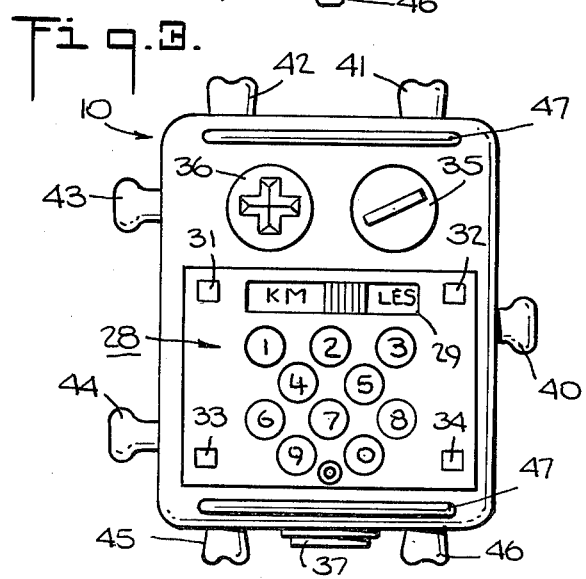
FIG. 3 shows the reverse side of the pacing timer.

FIG. 3 shows the reverse side of the pacing timer 10 which is adjacent and connected to the mounting pad 15 of FIG. 1. There is seen a keyboard 28 for entering numerical information into the internal memory of the pacing timer. It will be noted that the keyboard is not accessible to the runner once the unit has been mounted on mounting pad 15 but this, of course, is no drawback since the unit would not be mounted on pad 15 until the runner was prepared to commence the race and there would be no occasion for the runner to manipulate the keyboard 28 during the course of a race.

The keyboard unit 28 includes conversion switch 29 which can be set so that the unit can accept information in English or metric units. By setting conversion switch 29 to the "KM" (kilometer) setting all displayed information relating to distances would be in the kilometer mode while if conversion switch 29 were set to "miles" all distance information would be outputted in terms of this latter unit. The keyboard includes a decimal point key and identifying keys 31, 32, 33, and 34. Key 31 is activated to identify that the keyboard information to be next entered will be the split or race distance. Key 32 indicates that the keyboard information to be entered corresponds to the desired split time and key 33 corresponds to the stride length at a particular speed. Key 34 identifies that the keyboard information being entered corresponds to maximum pulse rate.

FIG. 3 also shows an electric battery compartment 35 and a control switch 36 actuating a magnetic tape recording device located inside the pacing timer 10. The magnetic tape recorder is of conventional construction for recording data on micro-cassette tapes or magnetic cards. Data to be so recorded includes the information inputted to the pacing timer before and during a race. The runner can then attempt to repeat his performance of that race by using the magnetically recorded information to actuate the display 24 and stride tone apparatus, all as described in detail in the above-identified copending application whose disclosure is incorporated herein by reference.

Figure 4:
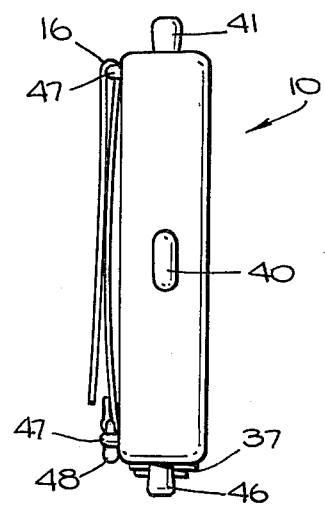
FIG. 4 shows a side view of the pacing timer.

As is seen in FIGS. 3 and 4, the pacing timer incorporates bars 47 for attaching strap 16 by means of double pins 48. Several pieces of elastomeric adhesive mate with the adhesive on mounting pad 15 and are secured to the strap to enable adhesion of the pacing timer 10 to the mounting pad 15 as seen in FIG. 1. The strap 16 can be removed by pushing pin 48 through bar 47.

Figure 5:
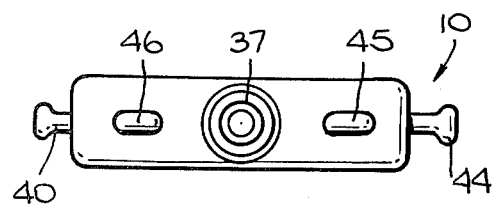
FIG. 5 shows the bottom view of the pacing timer.
Figure 5:
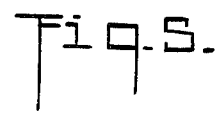

FIG. 5 shows an input 37 which is adapted to be connected to a pulse rate monitor unit so that pulse rate information can be fed to the pacing timer for further processing. In addition, other information could be fed to the pacing timer 10 via input 37 particularly if a portion of the computing circuitry were located in a unit separate from the pacing timer 10, such as, for example, a module carried at the runner's waist.

FIG. 6 shows another embodiment of mounting means (15a) for pacing timer 10. In this arrangement at least two flaps 50, 52, (and optionally four (50, 51, 52, 53)) are provided and are secured to the glove 12. Each flap has one or more holes 54 as required to accomodate the peripheral controls of pacing timer 10. The edges 55, 56, 57, 58 of each flap may be provided with elastomeric adhesive so that those edges may be detachably secured to the top edge portions of pacing timer 10; alternatively, the flap edges or some of them, may be interlocked by conventional snaps, zippers or other fastening means.

FIG. 7 shows another embodiment of mounting means (15b) for pacing timer 10. In the embodiment, glove 12 is provided with a compartment 15b secured to the glove along lines 60, 61, 62 and openable at zipper 63. Optionally, the compartment 15b can be opened and closed at location 63 by means of mating strips of elastomeric adhesive.

Since certain changes may be made in the above-described pacing timer and mounting arrangement therefor, without departing from the scope of the invention involved herein, and because the above-described mounting arrangement can be used to mount devices other than my pacing timer, without departing from the scope of the invention involved herein, it is intended that all matter contained in the above description or shown in the accompanying drawings shall be interpreted as illustrative and not in a limiting sense.

What is claimed is:

1. A pacing timer display mounting arrangement including in combination:
    (a) a glove piece worn between the wrist and at least index finger and thumb;
    (b) a mounting means for detachably mounting said pacing timer;
    (c) a pacing timer adapted to be detachably affixed to said glove piece by said mounting means, said timer including a face and reverse side with said reverse side being directed toward said wrist when said pacing timer is mounted on said glove piece;
    (d) said face of said pacing timer including a means for displaying information to the wearer;
    (e) said reverse side including an input means for entering information into the pacing timer.

2. A pacing timer display mounting arrangement including in combination:
    (a) a glove piece worn between the wrist and at least index finger and thumb;
    (b) a first mounting means for detachably mounting said pacing timer, said first mounting means being located on said glove piece at least partially between the knuckles of the index finger and thumb;
    (c) a pacing timer adapted to be detachably affixed to said glove piece by said first mounting means, said timer including a face and reverse side with said reverse side being directed toward said wrist when said pacing timer is mounted on said glove piece;
    (d) said face of said pacing timer including a means for displaying information to the wearer;
    (e) said reverse side including an input means for entering information into the pacing timer.

3. The pacing timer mounting arrangement in accordance with claim 2 wherein said pacing timer includes a plurality of terminals located at the timer periphery for controlling operations of said pacing timer.

4. The pacing timer mounting arrangement in accordance with claim 2 wherein said reverse side of said pacing timer includes a keyboard and a second mounting means detachably located over said keyboard and adapted to be affixed to said first mounting means.

5. The arrangement according to claim 4 wherein said second mounting means includes elastomeric adhesive.

6. The arrangement according to claims 2, 3, or 4 wherein said pacing timer includes at its periphery an input for information corresponding to the runner's pulse rate.

7. The arrangement according to claims 2, 3, or 4 wherein said first mounting means includes a plurality of flap means for forming a receiving compartment for said timer.

8. The arrangement according to claims 2, 3, or 4 wherein said first mounting means comprises a compartment means for receiving said timer.

9. An arrangement for mounting a timing device on a human hand, comprising:
    (a) a glove piece worn between the wrist, and index finger and thumb, and
    (b) mounting means for detachably mounting the timing device on said glove piece at least partially between the knuckles of the index finger and thumb.

10. The arrangement of claim 9 wherein said mounting means comprises a compartment means for receiving said timer.

11. The arrangement of claim 10 wherein said compartment means comprises a plurality of flap means.

12. An arrangement for mounting a timing device on a human hand, comprising:
    (a) a glove piece worn between the wrist, and at least index finger and thumb,
    (b) first mounting means disposed on said glove piece, and
    (c) second mounting means disposed on the timing device for detachably engaging said first mounting means.

* * * * *